United States Patent
Sawaki et al.

(10) Patent No.: US 12,359,028 B2
(45) Date of Patent: Jul. 15, 2025

(54) METHOD FOR PRODUCING WATER-ABSORBENT RESIN PARTICLES AND WATER-ABSORBENT RESIN PARTICLES

(71) Applicant: SUMITOMO SEIKA CHEMICALS CO., LTD., Hyogo (JP)

(72) Inventors: Hiroki Sawaki, Himeji (JP); Tomoka Yamamoto, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 129 days.

(21) Appl. No.: 17/757,137

(22) PCT Filed: Dec. 9, 2020

(86) PCT No.: PCT/JP2020/045931
§ 371 (c)(1),
(2) Date: Jun. 9, 2022

(87) PCT Pub. No.: WO2021/117785
PCT Pub. Date: Jun. 17, 2021

(65) Prior Publication Data
US 2023/0016075 A1    Jan. 19, 2023

(30) Foreign Application Priority Data

Dec. 13, 2019  (JP) .................................. 2019-225184
Dec. 13, 2019  (JP) .................................. 2019-225185
(Continued)

(51) Int. Cl.
*C08J 3/12*         (2006.01)
*B01J 20/24*        (2006.01)
(Continued)

(52) U.S. Cl.
CPC ............... *C08J 3/126* (2013.01); *B01J 20/24* (2013.01); *B01J 20/26* (2013.01); *B01J 20/261* (2013.01);
(Continued)

(58) Field of Classification Search
None
See application file for complete search history.

(56) References Cited

U.S. PATENT DOCUMENTS 4,727,097 A    2/1988  Kobayashi et al.
5,331,059 A    7/1994  Engelhardt et al.
(Continued)

FOREIGN PATENT DOCUMENTS

CN    102858815    1/2013
CN    103003313    3/2013
(Continued)

OTHER PUBLICATIONS

Machine translation WO-9937395-A1 (Year: 2024).*
(Continued)

*Primary Examiner* — Alexandre F Ferre
(74) *Attorney, Agent, or Firm* — HSML P.C.

(57) ABSTRACT

A first embodiment of a method for producing water-absorbent resin particles includes a polymerization step of polymerizing a monomer on at least a part of a surface of a surface-crosslinked polymer particle to obtain a polymer. A second embodiment of a method for producing water-absorbent resin particles includes a polymerization step of polymerizing a monomer on at least a part of a surface of a non-surface-crosslinked polymer particle in the presence of a crosslinking agent to obtain a polymer.

4 Claims, 1 Drawing Sheet

(30) Foreign Application Priority Data

| Feb. 19, 2020 | (JP) | 2020-026078 |
|---|---|---|
| May 14, 2020 | (JP) | 2020-085218 |
| May 14, 2020 | (JP) | 2020-085220 |
| May 14, 2020 | (JP) | 2020-085224 |
| May 14, 2020 | (JP) | 2020-085226 |
| May 14, 2020 | (JP) | 2020-085227 |
| Jul. 17, 2020 | (JP) | 2020-122800 |

(51) Int. Cl.
| *B01J 20/26* | (2006.01) |
|---|---|
| *B01J 20/28* | (2006.01) |
| *C08F 2/08* | (2006.01) |
| *C08F 20/06* | (2006.01) |
| *C08F 120/06* | (2006.01) |
| *C08G 65/08* | (2006.01) |
| *C08J 3/16* | (2006.01) |
| *C08L 33/26* | (2006.01) |
| *C08L 101/14* | (2006.01) |

(52) U.S. Cl.
CPC ........... *B01J 20/262* (2013.01); *B01J 20/264* (2013.01); *B01J 20/265* (2013.01); *B01J 20/28* (2013.01); *B01J 20/28016* (2013.01); *C08F 2/08* (2013.01); *C08F 20/06* (2013.01); *C08F 120/06* (2013.01); *C08G 65/08* (2013.01); *C08J 3/16* (2013.01); *C08L 33/26* (2013.01); *C08L 101/14* (2013.01)

(56) References Cited

U.S. PATENT DOCUMENTS

| 5,731,365 | A | 3/1998 | Engelhardt et al. | |
|---|---|---|---|---|
| 9,982,069 | B2 * | 5/2018 | Hinayama | A61L 15/60 |
| 2008/0269372 | A1 * | 10/2008 | Dairoku | C08J 3/243 |
| | | | | 523/149 |
| 2009/0105389 | A1 | 4/2009 | Walden et al. | |
| 2019/0217272 | A1 | 7/2019 | Hong et al. | |

FOREIGN PATENT DOCUMENTS

| CN | 103154043 | | 6/2013 | |
|---|---|---|---|---|
| CN | 103261235 | | 8/2013 | |
| CN | 104203988 | | 12/2014 | |
| CN | 105408365 | | 3/2016 | |
| CN | 105517660 | | 4/2016 | |
| DE | 4138408 | | 5/1993 | |
| EP | 0543303 | | 5/1993 | |
| EP | 0703265 | B1 | 9/2001 | |
| EP | 1510229 | | 3/2005 | |
| EP | 2535361 | | 12/2012 | |
| JP | 57168921 | A * | 10/1982 | |
| JP | S60-036516 | | 2/1985 | |
| JP | H1-126314 | | 5/1989 | |
| JP | 11347402 | A * | 12/1999 | |
| JP | H11-347402 | | 12/1999 | |
| JP | 2003-088553 | | 3/2003 | |
| JP | 2005-097585 | | 4/2005 | |
| JP | 2009-035657 | | 2/2009 | |
| JP | 2013-203761 | | 10/2013 | |
| JP | 2013-213083 | | 10/2013 | |
| JP | 2014-098172 | | 5/2014 | |
| JP | 2016-069418 | | 5/2016 | |
| JP | 2016-112474 | | 6/2016 | |
| WO | WO-9937395 | A1 * | 7/1999 | ............ C08F 251/00 |
| WO | 2006/062253 | | 6/2006 | |

OTHER PUBLICATIONS

Machine translation JP2013-213083 (Year: 2024).*
Machine translation JP H11347402 (Year: 2025).*
Machine translation JP-57168921-A (Year: 2025).*
International Search Report of PCT/JP2020/045931, Mar. 16, 2021, 2 pages.
International Preliminary Report on Patentability of PCT/JP2020/045931, Jun. 23, 2022, 6 pages.
The extended European search report issued for European Patent Application No. 20900116.3, Jan. 9, 2024, 13 pages.

* cited by examiner

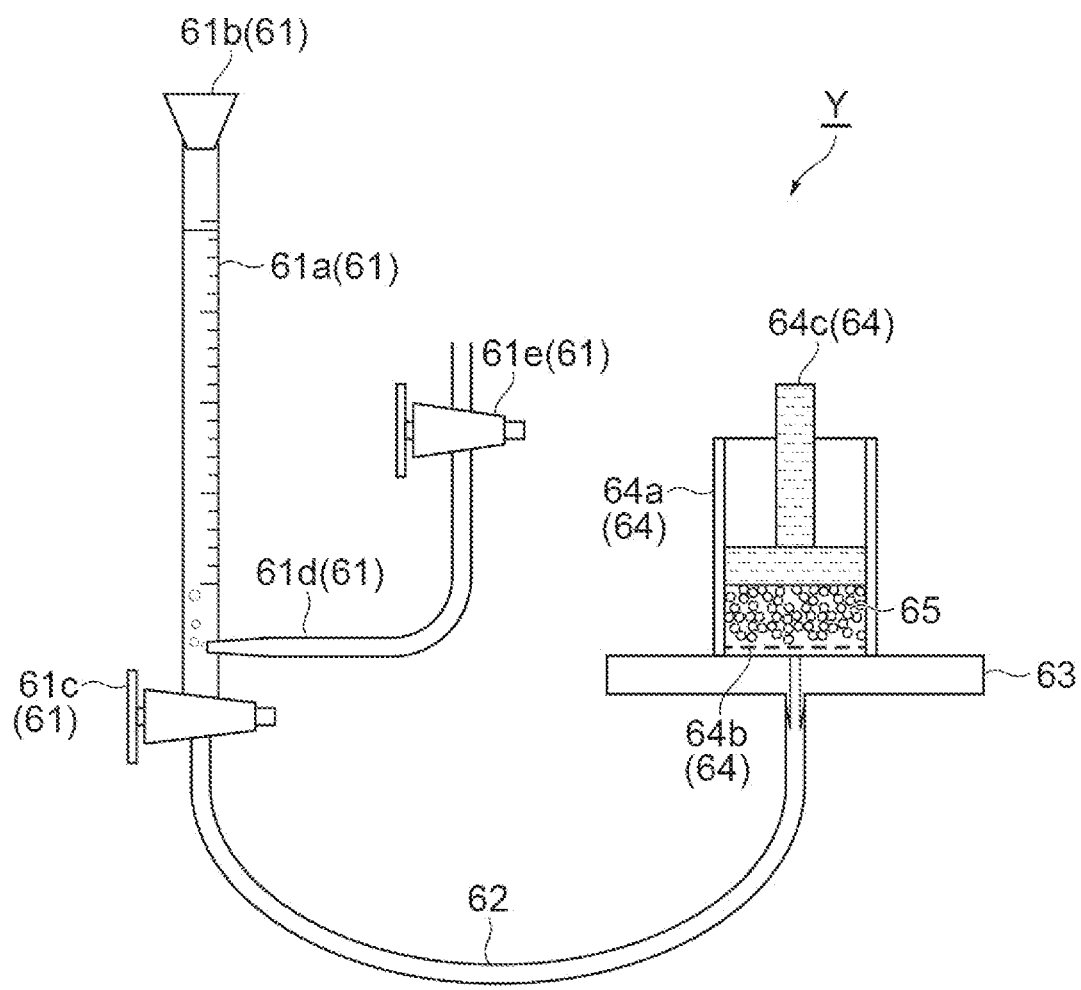

METHOD FOR PRODUCING WATER-ABSORBENT RESIN PARTICLES AND WATER-ABSORBENT RESIN PARTICLES

TECHNICAL FIELD

The present invention relates to a method for producing water-absorbent resin particles, a water-absorbent resin particle, and the like.

BACKGROUND ART

Water-absorbent resin particles are widely used in various fields of sanitary materials such as disposable diapers, hygiene products, and portable toilets; agricultural and horticultural materials such as water retention agents and soil improvement agents; and industrial materials such as waterproofing agents and condensation prevention agents. When manufacturing sanitary materials, water-absorbent resin particles are damaged due to collisions between the water-absorbent resin particles, friction with machines, or the like, and there is a possibility of the loss of the original water absorption performance. Regarding such a problem, a technique of improving impact resistance and the like by controlling the internal air bubble ratio of the water-absorbent resin particles is known (refer to Patent Literature 1 below, for example).

CITATION LIST

Patent Literature

[Patent Literature 1] Japanese Unexamined Patent Publication No. 2014-098172

SUMMARY OF INVENTION

Technical Problem

According to the findings of the inventor of the present invention, it is difficult to improve impact resistance while achieving excellent water absorption performance under load in the related art regarding water-absorbent resin particles.

The purpose of one aspect of the present invention is to provide a method for producing water-absorbent resin particles capable of improving impact resistance while achieving better water absorption performance under load (equal to or higher level of water absorption performance) in comparison of methods for producing water-absorbent resin particles in which raw materials of the same details are used. The purpose of another aspect of the present invention is to provide water-absorbent resin particles capable of improving impact resistance while achieving better water absorption performance under load in comparison of water-absorbent resin particles obtained using raw materials of the same details.

Solution to Problem

The inventor of the present invention found the following findings. That is, they thought of performing surface crosslinking on polymer particles as a technique of improving water absorption performance under load. However, performing only surface crosslinking does not sufficiently improve the water absorption performance under load in some cases, and also is likely to cause damage of water-absorbent resin particles (low impact resistance) in some cases. On the other hand, by performing treatment in which polymer particles are subjected to surface crosslinking and thereafter a monomer is polymerized on the surface of the polymer particles, or treatment in which a monomer is polymerized on the surface of non-surface-crosslinked polymer particles in the presence of a crosslinking agent, impact resistance can be improved while achieving better water absorption performance under load (water absorption performance under load) as compared to the case in which these treatments are not performed, in comparison of the methods for producing water-absorbent resin particles in which raw materials of the same details are used.

A first embodiment of a method for producing water-absorbent resin particles of one aspect of the present invention includes a polymerization step of polymerizing a monomer on at least a part of a surface of a surface-crosslinked polymer particle to obtain a polymer.

A second embodiment of a method for producing water-absorbent resin particles of one aspect of the present invention includes a polymerization step of polymerizing a monomer on at least a part of a surface of a non-surface-crosslinked polymer particle in the presence of a crosslinking agent to obtain a polymer.

According to these methods for producing water-absorbent resin particles, water-absorbent resin particles capable of improving impact resistance while achieving better water absorption performance under load can be obtained as compared to the case in which these polymerization steps are not performed, in comparison of the methods for producing water-absorbent resin particles in which raw materials of the same details are used.

A water-absorbent resin particle of another aspect of the present invention contains a surface-crosslinked polymer particle, and a polymer disposed on at least a part of a surface of the polymer particle.

According to such water-absorbent resin particles, impact resistance can be improved while achieving better water absorption performance under load in comparison of the water-absorbent resin particles obtained using raw materials of the same details.

Advantageous Effects of Invention

According to one aspect of the present invention, it is possible to provide a method for producing water-absorbent resin particles capable of improving impact resistance while achieving better water absorption performance under load in comparison of methods for producing water-absorbent resin particles in which raw materials of the same details are used. According to another aspect of the present invention, it is possible to provide water-absorbent resin particles capable of improving impact resistance while achieving better water absorption performance under load in comparison of water-absorbent resin particles obtained using raw materials of the same details.

BRIEF DESCRIPTION OF DRAWINGS

FIG. 1 is a schematic view showing a measurement device of a water absorption amount under load of water-absorbent resin particles.

DESCRIPTION OF EMBODIMENTS

Hereinafter, embodiments of the present invention will be described in detail. However, the present invention is not limited to the following embodiments, and can be variously modified within the scope of the gist thereof and implemented.

In the present specification, "acrylic" and "methacryl" are collectively referred to as "(meth)acrylic". Similarly, "acrylate" and "methacrylate" are also referred to as "(meth) acrylate". "(Poly)" means both of a case where there is a prefix of "poly" and a case where there is no prefix thereof. Regarding numerical value ranges described in a stepwise manner in the present specification, the upper limit value or the lower limit value of a numerical value range in a certain step can be arbitrarily combined with the upper limit value or the lower limit value of a numerical value range in another step. In a numerical value range described in the present specification, the upper limit value or the lower limit value of the numerical value range may be replaced with the value shown in Examples. Room temperature means 25° C.±2° C. For materials exemplified in the present specification, one kind may be used alone, or two or more kinds may be used in combination. The content of each component in the composition means the total amount of a plurality of substances present in the composition in a case where the plurality of substances corresponding to each component are present in the composition, unless otherwise specified.

A method for producing water-absorbent resin particles of a first embodiment includes a polymerization step of polymerizing a monomer on at least a part of a surface of a surface-crosslinked polymer particle to obtain a polymer. A method for producing water-absorbent resin particles of a second embodiment includes a polymerization step of polymerizing a monomer on at least a part of a surface of a non-surface-crosslinked polymer particle in the presence of a crosslinking agent to obtain a polymer. In the polymerization step, as the polymer of the monomer, a polymer disposed on at least a part of the surface of the polymer particle can be obtained.

According to the method for producing water-absorbent resin particles of the present embodiment (including the first embodiment and the second embodiment), by performing treatment in which polymer particles are subjected to surface crosslinking and thereafter a monomer is polymerized on the surface of the polymer particles, or treatment in which a monomer is polymerized on the surface of non-surface-crosslinked polymer particles in the presence of a crosslinking agent, water-absorbent resin particles capable of improving impact resistance while achieving better water absorption performance under load (under pressurization) can be obtained as compared to a case in which these treatments are not performed, in comparison of methods for producing water-absorbent resin particles in which raw materials of the same details (the same type, the same amount, and the like) are used. According to the method for producing water-absorbent resin particles of the present embodiment, the impact resistance can be improved while achieving better water absorption performance under load by adjusting the order of polymerization of the monomer and use of the crosslinking agent.

The water-absorbent resin particle of the present embodiment contains a surface-crosslinked polymer particle, and a polymer disposed on at least a part of a surface of the polymer particle. Such water-absorbent resin particles can be obtained by the method for producing water-absorbent resin particles of the first embodiment. According to the water-absorbent resin particle of the present embodiment, the impact resistance can be improved while achieving better water absorption performance under load in comparison of water-absorbent resin particles obtained using raw materials of the same details.

According to the water-absorbent resin particle and the method for producing the same of the present embodiment, by improving the impact resistance, generation of particles having a small particle diameter when pressure is applied to the water-absorbent resin particle can be prevented.

The inventor of the present invention presumes that the impact resistance is improved while achieving better water absorption performance under load due in part to the following mechanism. That is, when polymer particles are subjected to surface crosslinking, the crosslinking density on the surface thereof is increased, and thereby a hard layer is obtained as an outermost layer. In this case, even when better water absorption performance under load is obtained, the hard outermost layer is likely to be damaged by the collision between the particles (low impact resistance).

On the other hand, according to the method for producing water-absorbent resin particles of the first embodiment, by polymerizing the monomer on the surface of the polymer particles after subjecting the polymer particles to surface crosslinking, a hard layer obtained by performing surface crosslinking can be prevented from being exposed as an outermost layer while maintaining the state in which the polymer particles are surface-crosslinked. Accordingly, the impact resistance can be improved while achieving better water absorption performance under load.

Furthermore, according to the method for producing water-absorbent resin particles of the second embodiment, by polymerizing the monomer on the surface of the non-surface-crosslinked polymer particles in the presence of the crosslinking agent, crosslinking of an outermost layer is promoted while preventing an excessive increase of the crosslinking density of the outermost layer, and thereby the impact resistance can be improved while achieving better water absorption performance under load.

However, the mechanism by which the effect is exhibited is not limited to these contents.

The median particle diameter of the water-absorbent resin particles of the present embodiment may be in the following range. The median particle diameter of the water-absorbent resin particles may be 100 μm or more, 150 μm or more, 200 μm or more, 250 μm or more, 300 μm or more, 350 μm or more, 360 μm or more, 370 μm or more, 380 μm or more, 400 μm or more, 420 μm or more, or 450 μm or more. The median particle diameter of the water-absorbent resin particles may be 800 μm or less, 700 μm or less, 600 μm or less, 500 μm or less, 450 μm or less, 420 μm or less, 400 μm or less, 380 μm or less, 370 μm or less, or 360 μm or less. From these viewpoints, the median particle diameter of the water-absorbent resin particles may be 100 to 800 μm.

In the polymerization step of the method for producing water-absorbent resin particles of the first embodiment, the monomer is polymerized on at least a part of the surface of the surface-crosslinked polymer particle. The "surface-crosslinked polymer particle" is a polymer particle in which the crosslinking density on the surface is higher than that inside the particle.

In the polymerization step of the method for producing water-absorbent resin particles of the first embodiment, the monomer is brought into contact with the surface of the polymer particle. In the polymerization step, the monomer may be added to a liquid containing the polymer particles, or a liquid containing the polymer particles and a liquid containing the monomer may be mixed. In the polymerization step, the monomer is polymerized in the state in which the crosslinking agent is not present. The liquid containing the monomer does not contain the crosslinking agent. The "state in which the crosslinking agent is not present" is synonymous with no addition of the crosslinking agent in the polymerization step. When an internal crosslinking agent is used to form the polymer particles, there is a possibility of leaking of a very small amount of the internal crosslinking agent remaining in the polymer particles to the outside of the polymer particles during the polymerization step, but this case is also included in the "state in which the crosslinking agent is not present", if the crosslinking agent is not newly added in the polymerization step.

In the polymerization step of the method for producing water-absorbent resin particles of the second embodiment, the monomer is polymerized on at least a part of the surface of the non-surface-crosslinked polymer particle in the presence of the crosslinking agent. The "non-surface-crosslinked polymer particle" is a polymer particle in which the crosslinking density inside the particle and the crosslinking density on the surface are substantially equivalent.

In the polymerization step of the method for producing water-absorbent resin particles of the second embodiment, the monomer and the crosslinking agent are brought into contact with the surface of the polymer particle. The monomer and the crosslinking agent may be added to a liquid containing the polymer particles, a liquid containing the polymer particles and a liquid containing the monomer and the crosslinking agent may be mixed, or a liquid containing the polymer particles, a liquid containing the monomer, and a liquid containing the crosslinking agent may be mixed.

The shape of the polymer particle is not particularly limited, and may be substantially spherical, amorphous, granular, or the like, and may be a shape in which primary particles having these shapes are aggregated, for example. The amorphous polymer particle can be obtained by crushing a mass of a polymer with a crusher, for example.

The polymer particle may have water absorption properties. The water absorption amount (water absorption amount under normal pressure) of ion-exchanged water at 25° C. in the polymer particle may be 10 g/g or more, for example.

The polymer particle may contain a gel stabilizer, a metal chelating agent, a flowability improver (lubricant), and the like. These components may be disposed inside the polymer particle, or on the surface of the polymer particle, or inside and on the surface thereof.

The polymer obtained in the polymerization step may be water-soluble, and may not be water-soluble (may be poorly water-soluble). When the polymer is water-soluble, the solubility of the polymer may be 1 g or more (for example, 1 to 150 g) with respect to 100 g of ion-exchanged water at 25° C., for example. When the polymer is poorly water-soluble, the solubility of the polymer may be less than 1 g with respect to 100 g of ion-exchanged water at 25° C., for example.

The polymer obtained in the polymerization step may constitute a cover part that covers at least a part of the surface of the polymer particle (coated body). The cover part covers a part or the whole of the surface of the polymer particle as long as it covers at least a part of the surface of the polymer particle. In the water-absorbent resin particles of the present embodiment, the crosslinking density of the cover part may be lower than the crosslinking density of the surface of the polymer particle.

The reaction temperature in the polymerization step may be 15° C. to 200° C., for example. The polymerization reaction in the polymerization step may be a chain polymerization reaction, a sequential polymerization reaction, or the like. Examples of constituent materials of the polymer obtained in the polymerization step include chain polymerization reaction products such as poly(meth)acrylic acid, poly(meth)acrylamide, polyvinyl alcohol, polyalkylene oxide, and polyalkylene glycol; and sequential polymerization reaction product such as polyurethane (urethane resin), phenolic resin (for example, a condensate of a phenolic compound and an aldehyde), polyester, polyamide, and poly carbonate. The polymer may be a crosslinking polymer.

The polymer obtained in the polymerization step preferably includes a polymer having a structural unit derived from an ethylenically unsaturated monomer (a polymer having an ethylenically unsaturated monomer as a monomeric unit) from the viewpoint of easily improving the impact resistance while achieving better water absorption performance under load. The polymer obtained in the polymerization step preferably contains polyurethane from the viewpoint of easily improving the impact resistance while achieving better water absorption performance under load.

Examples of the ethylenically unsaturated monomer include (meth)acrylic acid and salts thereof, (meth)acrylic acid esters (methyl (meth)acrylate, ethyl (meth)acrylate, 2-hydroxyethyl (meth)acrylate, 2-(diethylamino)ethyl (meth)acrylate, 2-(diethylamino)propyl (meth)acrylate, and the like), (meth)acrylamide-based monomers ((meth)acrylamide, N-isopropyl(meth)acrylamide, 2-(meth)acrylamide-2-methylpropanesulfonic acid and salts thereof, N,N-dimethyl(meth)acrylamide, N-methylol(meth)acrylamide, diethylaminopropyl (meth)acrylamide, and the like), and polyethylene glycol mono(meth)acrylate. The ethylenically unsaturated monomer preferably includes at least one selected from the group consisting of (meth)acrylic acid and salts thereof from the viewpoint of easily improving the impact resistance while achieving better water absorption performance under load. The ethylenically unsaturated monomer preferably includes a (meth)acrylamide-based monomer from the viewpoint of easily improving the impact resistance while achieving better water absorption performance under load.

In the polymerization step, when a plurality of substances are reacted with each other to obtain a polymer, examples of combinations of the plurality of substances include polyols and polyisocyanates; aldehydes and phenolic compounds; polyols and polycarboxylic acids; polyamines and polycarboxylic acids; phenolic compounds and carbonic acid esters; and phenolic compounds and chlorocarbonic acid.

The polyol may be any compound as long as it has two or more hydroxyl groups, and diols, viols, or the like can be used. Examples of the polyols include polyether polyols, polyester polyols, polycarbonate polyols, polysiloxane polyols, polyisoprene polyols, and polyolefin polyols.

The polyisocyanate may be any compound as long as it has two or more isocyanate groups, and diisocyanate, triisocyanate, or the like can be used. Examples of the polyisocyanates include aromatic isocyanates such as diphenylmethane diisocyanate, dimethyldiphenylmethane diisocyanate, tolylene diisocyanate (for example, tolylene-2,4-diisocyanate), xylylene diisocyanate, and p-phenylene diisocyanate; alicyclic isocyanates such as dicyclohexylmethane diisocyanate and isophorone diisocyanate; and aliphatic isocyanates such as hexamethylene diisocyanate.

Examples of the aldehydes include aliphatic aldehydes such as formaldehyde, acetaldehyde, and propionaldehyde; and aromatic aldehydes such as benzaldehyde.

Examples of the phenolic compounds include phenol, cresol, catechol, naphthol, and hydroquinone.

From the viewpoint of easily obtaining excellent impact resistance, and from the viewpoint of easily improving a water absorption amount under load and/or impact resistance in comparison of the methods for producing water-absorbent resin particles in which raw materials of the same details are used, the amount of the monomer in the polymerization step of the method for producing water-absorbent resin particles of the present embodiment with respect to 100 mol of the monomer used to obtain the polymer particles in a particle production step to be described later (in the case of multi-stage polymerization, the total amount of the monomer of each stage) is preferably in the following range. The amount of the monomer is preferably 0.01 mol or more, 0.05 mol or more, 0.1 mol or more, 0.5 mol or more, 1 mol or more, 2 mol or more, 5 mol or more, 10 mol or more, 11 mol or more, 12 mol or more, 13 mol or more, 14 mol or more, 15 mol or more, 20 mol or more, 25 mol or more, 30 mol or more, 40 mol or more, or 50 mol or more. The amount of the monomer is preferably 100 mol or less, less than 100 mol, 80 mol or less, 60 mol or less, 50 mol or less, 40 mol or less, 30 mol or less, 25 mol or less, 20 mol or less, 15 mol or less, 14 mol or less, 13 mol or less, 12 mol or less, 11 mol or less, 10 mol or less, 5 mol or less, 2 mol or less, 1 mol or less, 0.5 mol or less, or 0.1 mol or less. From these viewpoints, the amount of the monomer is preferably 0.01 to 100 mol.

Examples of the crosslinking agent in the polymerization step of the method for producing water-absorbent resin particles of the second embodiment include polyglycidyl compounds such as (poly)ethylene glycol diglycidyl ether, (poly)propylene glycol diglycidyl ether, (poly)glycerin diglycidyl ether, (poly)glycerin triglycidyl ether, (poly)propylene glycol polyglycidyl ether, and polyglycerol polyglycidyl ether.

From the viewpoint of easily improving the impact resistance while achieving better water absorption performance under load, the amount of the crosslinking agent in the polymerization step of the method for producing water-absorbent resin particles of the second embodiment with respect to 100 mol of the monomer in the polymerization step is preferably in the following range. The amount of the crosslinking agent is preferably 0.001 mol or more, more preferably 0.003 mol or more, further preferably 0.005 mol or more, particularly preferably 0.008 mol or more, extremely preferably 0.01 mol or more, and extraordinarily preferably 0.02 mol or more. The amount of the crosslinking agent is preferably 1 mol or less, more preferably 0.5 mol or less, further preferably 0.1 mol or less, particularly preferably 0.05 mol or less, and extremely preferably 0.03 mol or less. From these viewpoints, the amount of the crosslinking agent is preferably 0.001 to 1 mol.

The method for producing water-absorbent resin particles of the second embodiment does not include a surface crosslinking step of surface-crosslinking the polymer particles before the polymerization step. The method for producing water-absorbent resin particles of the first embodiment may include the surface crosslinking step of surface-crosslinking the polymer particles before the polymerization step. In the surface crosslinking step, the polymer particles are surface-crosslinked by mixing the polymer particles and a surface crosslinking agent. The surface crosslinking step may not involve polymerization of the monomer.

Examples of the surface crosslinking agent include polyglycidyl compounds such as (poly)ethylene glycol diglycidyl ether, (poly)propylene glycol diglycidyl ether, (poly)glycerin diglycidyl ether, (poly)glycerin triglycidyl ether, (poly)propylene glycol polyglycidyl ether, and polyglycerol polyglycidyl ether.

From the viewpoint of easily improving the impact resistance while achieving better water absorption performance under load, the amount of the surface crosslinking agent in the surface crosslinking step with respect to 100 mol (in the case of multi-stage polymerization, the total amount of the monomer of each stage) of the monomer used for obtaining the polymer particles is preferably in the following range. The amount of the surface crosslinking agent is preferably 0.0005 mol or more, more preferably 0.001 mol or more, and further preferably 0.002 mol or more. The amount of the surface crosslinking agent is preferably 0.5 mol or less, more preferably 0.1 mol or less, and further preferably 0.05 mol or less.

The method for producing water-absorbent resin particles of the present embodiment may include the particle production step of polymerizing the monomer to obtain the polymer particles before the surface crosslinking step and the polymerization step. In the particle production step, the monomer can be polymerized once or multiple times.

The polymer particles can be obtained by polymerizing the monomer including the ethylenically unsaturated monomer, for example. That is, the polymer particles can have a structural unit derived from the ethylenically unsaturated monomer (have the ethylenically unsaturated monomer as a monomeric unit). Examples of a polymerization method of the ethylenically unsaturated monomer include a reverse phase suspension polymerization method, an aqueous solution polymerization method, a bulk polymerization method, and a precipitation polymerization method.

The ethylenically unsaturated monomer may be a water-soluble ethylenically unsaturated monomer (for example, an ethylenically unsaturated monomer having the solubility of 1 g or more in 100 g of ion-exchanged water at 25° C.). Examples of the ethylenically unsaturated monomer include (meth)acrylic acid and salts thereof, (meth)acrylic acid esters (methyl (meth)acrylate, ethyl (meth)acrylate, 2-hydroxyethyl (meth)acrylate, 2-(diethylamino)ethyl (meth)acrylate, 2-(diethylamino)propyl (meth)acrylate, and the like), (meth)acrylamide-based monomers ((meth)acrylamide, N-isopropyl(meth)acrylamide, 2 (meth)acrylamide-2-methylpropanesulfonic acid and salts thereof, N,N-dimethyl(meth)acrylamide, N-methylol(meth)acrylamide, diethylaminopropyl (meth)acrylamide, and the like), and polyethylene glycol mono(meth)acrylate. The ethylenically unsaturated monomer may include at least one selected from the group consisting of (meth)acrylic acid and salts thereof from the viewpoint of easily obtaining the water-absorbent resin particles while preventing aggregation of the particles. The polymer particles preferably have a structural unit derived from at least one selected from the group consisting of (meth)acrylic acid and salts thereof from the viewpoint of easily obtaining the water-absorbent resin particles while preventing aggregation of the particles.

When the ethylenically unsaturated monomer has an acid group, the acid group may be neutralized and then used in the polymerization reaction. The degree of neutralization in the ethylenically unsaturated monomer may be 10 to 100 mol %, 50 to 90 mol %, or 60 to 80 mol % of the acid group in the ethylenically unsaturated monomer.

As the monomer for obtaining the polymer particles, a monomer other than the above-mentioned ethylenically unsaturated monomer may be used. Such a monomer can be used by being mixed with an aqueous solution containing the above-mentioned ethylenically unsaturated monomer, for example. The use amount of the ethylenically unsaturated monomer is preferably 70 to 100 mol % with respect to the total amount of the monomer (the total amount of the monomer for obtaining the polymer particles, for example, the total amount of the monomer that gives the structural unit of the crosslinking polymer, the same applies hereinafter). Among them, the ratio of (meth)acrylic acid and salts thereof is more preferably 70 to 100 mol % with respect to the total amount of the monomer. The "ratio of (meth)acrylic acid and salts thereof" means the ratio of the total amount of (meth)acrylic acid and salts thereof.

The internal crosslinking agent may be used for obtaining the polymer particles. When the internal crosslinking agent is used in the polymerization of the monomer, it is easy to increase the crosslinking density substantially uniformly in almost all the polymer particles. Examples of the internal crosslinking agent include polyglycidyl compounds such as (poly)ethylene glycol diglycidyl ether, (poly)propylene glycol diglycidyl ether, (poly)glycerin diglycidyl ether, (poly)glycerin triglycidyl ether, (poly)propylene glycol polyglycidyl ether, and polyglycerol polyglycidyl ether; divinyl-based compounds; dialcohol-based compounds; and diacrylate-based compounds.

The method for producing water-absorbent resin particles of the present embodiment may include a step of classifying the water-absorbent resin particles by a sieve after the polymerization step. This makes it possible to adjust particle size distribution.

According to the present embodiment, a liquid absorbing method using the water-absorbent resin particles of the present embodiment can be provided. The liquid absorbing method of the present embodiment includes a step of bringing a liquid to be absorbed into contact with the water-absorbent resin particles of the present embodiment.

EXAMPLES

Hereinafter, the contents of the present invention will be further described using Examples and Comparative Examples, but the present invention is not limited to the following Examples.

Example 1

A round-bottomed cylindrical separable flask with the inner diameter of 11 cm and the volume of 2 L equipped with a reflux cooling device, a dropping funnel, a nitrogen gas introduction tube, and a stirrer (a stirrer blade having two stages of four inclined paddle blades having the blade diameter of 5 cm) was prepared. To this separable flask, 293 g of n-heptane (hydrocarbon dispersion medium) and 0.736 g of a maleic anhydride-modified ethylene-propylene copolymer (polymeric dispersant, Mitsui Chemicals, Inc., Hi-Wax 1105A) were added to obtain a mixture. The dispersant was dissolved by heating to 80° C. while stirring this mixture at the rotation speed of 300 rpm, and thereafter the mixture was cooled to 55° C.

Subsequently, 92.0 g (acrylic acid: 1.03 mol) of an aqueous solution of 80.5% by mass acrylic acid was put to a triangular flask having the volume of 500 mL. Subsequently, while cooling from the outside, 102.2 g of an aqueous solution of 30% by mass sodium hydroxide was added dropwise to neutralize 75 mol % of acrylic acid. Thereafter, 0.092 g of hydroxyethyl cellulose (thickener, Sumitomo Seika Chemicals Co., Ltd., HEC AW 15F), 0.0736 g (0.272 mmol) of potassium persulfate (water-soluble radical polymerization initiator), 0.0101 g (0.0581 mmol) of ethylene glycol diglycidyl ether (internal cross-linking agent), and 32.85 g of ion-exchanged water were added and then dissolved to prepare a first stage monomer aqueous solution.

Then, the above-mentioned first stage monomer aqueous solution was added into the above-mentioned separable flask, and thereafter stirring was performed for 10 minutes. Thereafter, a reaction solution was obtained by adding, into the separable flask, 7.356 g of a surfactant solution obtained by heat-dissolving 0.736 g of sucrose stearic acid ester (surfactant, Mitsubishi-Chemical Foods Corporation, Ryoto Sugar Ester S-370, HLB: 3) in 6.62 g of n-heptane. Then, the inside of the system was sufficiently replaced with nitrogen while stirring the reaction solution at the rotation speed of 550 rpm. Thereafter, the separable flask was immersed in a water bath at 70° C. to raise the temperature of the reaction solution, and first stage polymerization was performed for 10 minutes to obtain a first stage reaction mixture.

Subsequently, 128.8 g (acrylic acid: 1.44 mol) of an aqueous solution of 80.5% by mass acrylic acid was put to another triangular flask having the volume of 500 mL. Subsequently, while cooling from the outside, 143.1 g of an aqueous solution of 30% by mass sodium hydroxide was added dropwise to neutralize 75 mol % of acrylic acid. Thereafter, 0.1030 g (0.3812 mmol) of potassium persulfate, 0.0116 g (0.0655 mmol) of ethylene glycol diglycidyl ether (internal crosslinking agent), and 0.63 g of ion-exchanged water were added and then dissolved to prepare a second stage monomer aqueous solution.

Then, cooling to 25° C. was performed while stirring the above-mentioned first stage reaction mixture at the rotation speed of 1000 rpm, and then the total amount of the above-mentioned second stage monomer aqueous solution was added to the first stage reaction mixture to obtain a reaction solution. Then, the inside of the system was sufficiently replaced with nitrogen while stirring the reaction solution. Thereafter, the separable flask was immersed in a water bath at 70° C. to raise the temperature of the reaction solution, and second stage polymerization was performed for 5 minutes to obtain a second stage reaction mixture (polymer particles before surface crosslinking).

After the second stage polymerization, the temperature of the second stage reaction mixture was raised in an oil bath at 125° C., and 267 g of water was extracted to the outside of the system while refluxing n-heptane by azeotropic distillation of n-heptane and water. Subsequently, 0.0884 g (0.5075 mmol) of ethylene glycol diglycidyl ether was added as a surface crosslinking agent, and thereafter the mixture was maintained at 83° C. for 2 hours to obtain a dispersion liquid of the polymer particles after surface crosslinking.

Subsequently, 111.4 g (acrylic acid: 1.25 mol) of an aqueous solution of 80.5% by mass acrylic acid was put to another triangular flask having the volume of 500 mL. Subsequently, while cooling from the outside, 125.8 g of an aqueous solution of 30% by mass sodium hydroxide was added dropwise to neutralize 75 mol % of acrylic acid. Thereafter, 0.0891 g (0.3296 mmol) of potassium persulfate and 0.84 g of ion-exchanged water were added, and then potassium persulfate was dissolved to prepare a third stage monomer aqueous solution.

Then, the above-mentioned dispersion liquid of the polymer particles after surface crosslinking was maintained at 83° C. for 2 hours, and then air-cooled to 50° C. Subsequently, the total amount of the above-mentioned third stage monomer aqueous solution was added to the dispersion liquid of the polymer particles after surface crosslinking to obtain a reaction solution. Then, the inside of the system was sufficiently replaced with nitrogen while stirring the reaction solution, and then the reaction solution was maintained at 45° C. for 30 minutes. Furthermore, the separable flask was immersed in a water bath at 75° C. to raise the temperature, and third stage polymerization was performed for 15 minutes to obtain a third stage reaction mixture.

After the third stage polymerization, the temperature of the third stage reaction mixture was raised in an oil bath at 125° C., water was extracted to the outside of the system until the temperature inside the flask reached 90° C. while refluxing n-heptane by azeotropic distillation of n heptane and water, and thereafter drying was performed by evaporating n-heptane to obtain a polymerization product. This polymerization product was passed through a sieve having the opening of 850 μm to obtain 282.62 g of water-absorbent resin particles in the form of aggregated spherical particles. The median particle diameter of the water-absorbent resin particles was 436 μm.

Comparative Example 1

Water-absorbent resin particles were produced in the same manner as in Example 1 except that, in Comparative Example 1, after obtaining a second stage reaction mixture (polymer particles before surface crosslinking), third stage polymerization and surface crosslinking were performed in this order instead of performing surface crosslinking before the third stage polymerization.

First, the production was performed in the same manner as in Example 1 up to second stage polymerization.

After the second stage polymerization, the temperature of the second stage reaction mixture was raised in an oil bath at 125° C., and 245 g of water was extracted to the outside of the system while refluxing n-heptane by azeotropic distillation of n-heptane and water.

Subsequently, 111.4 g (acrylic acid: 1.25 mol) of an aqueous solution of 80.5% by mass acrylic acid was put to a triangular flask having the volume of 500 mL. Subsequently, while cooling from the outside, 125.8 g of an aqueous solution of 30% by mass sodium hydroxide was added dropwise to neutralize 75 mol % of acrylic acid. Thereafter, 0.0891 g (0.3296 mmol) of potassium persulfate and 0.84 g of ion-exchanged water were added, and then potassium persulfate was dissolved to prepare a third stage monomer aqueous solution.

Then, the above-mentioned second stage reaction mixture (reaction mixture after extraction of water) was maintained at 83° C. for 2 hours, and then air-cooled to 50° C. Subsequently, the total amount of the above-mentioned third stage monomer aqueous solution was added to the second stage reaction mixture to obtain a reaction solution. Then, the inside of the system was sufficiently replaced with nitrogen while stirring the reaction solution, and then the reaction solution was maintained at 45° C. for 30 minutes. Furthermore, the separable flask was immersed in a water bath at 75° C. to raise the temperature, and the third stage polymerization was performed for 15 minutes to obtain a third stage reaction mixture.

After the third stage polymerization, the temperature of the third stage reaction mixture was raised in an oil bath at 125° C., and 204 g of water was extracted to the outside of the system while refluxing n-heptane by azeotropic distillation of n-heptane and water.

Thereafter, 0.0884 g (0.5075 mmol) of ethylene glycol diglycidyl ether was added as a surface crosslinking agent, and thereafter the mixture was maintained at 83° C. for 2 hours.

Then, drying was performed by evaporating n-heptane by raising the temperature in an oil bath at 125° C. to obtain a polymerization product. This polymerization product was passed through a sieve having the opening of 850 μm to obtain 283.36 g of water-absorbent resin particles in the form of aggregated spherical particles. The median particle diameter of the water-absorbent resin particles was 448 μm.

Example 2

217.07 g of water-absorbent resin particles (in the form of aggregated spherical particles) was obtained in the same manner as in Example 1 except that, in Example 2, the amount of water extracted after second stage polymerization was changed from 267 g to 241 g, and the details of a third stage monomer aqueous solution were changed. The third stage monomer aqueous solution was prepared as follows: 44.6 g (acrylic acid: 0.50 mol) of an aqueous solution of 80.5% by mass acrylic acid was put to a triangular flask having the volume of 500 mL; while cooling from the outside, 50.3 g of an aqueous solution of 30% by mass sodium hydroxide was added dropwise to neutralize 75 mol % of acrylic acid; and 0.0357 g (0.1319 mmol) of potassium persulfate and 0.5 g of ion-exchanged water were added, and then potassium persulfate was dissolved. The median particle diameter of the water-absorbent resin particles was 370 μm.

Comparative Example 2

216.32 g of water-absorbent resin particles was obtained in the same manner as in Comparative Example 1 except that, in Comparative Example 2, the amount of water extracted after second stage polymerization was changed from 245 g to 241 g, the details of a third stage monomer aqueous solution were changed, and the amount of water extracted after third stage polymerization was changed from 204 g to 42 g. The third stage monomer aqueous solution was prepared as follows: 44.6 g (acrylic acid: 0.50 mol) of an aqueous solution of 80.5% by mass acrylic acid was put to a triangular flask having the volume of 500 mL; while cooling from the outside, 50.3 g of an aqueous solution of 30% by mass sodium hydroxide was added dropwise to neutralize 75 mol % of acrylic acid; and 0.0357 g (0.1319 mmol) of potassium persulfate and 0.5 g of ion-exchanged water were added, and then potassium persulfate was dissolved. The median particle diameter of the water-absorbent resin particles was 386 μm.

Example 3

209.29 g of water-absorbent resin particles (in the form of aggregated spherical particles) was obtained in the same manner as in Example 1 except that, in Example 3, the details of a third stage monomer aqueous solution were changed, and the third stage monomer aqueous solution and a crosslinking agent were added at the same time.

First, the production was performed in the same manner as in Example 1 up to second stage polymerization.

Subsequently, 33.4 g (acrylic acid: 0.37 mol) of an aqueous solution of 80.5% by mass acrylic acid was put to a triangular flask having the volume of 500 mL. Subsequently, while cooling from the outside, 37.7 g of an aqueous solution of 30% by mass sodium hydroxide was added dropwise to neutralize 75 mol % of acrylic acid. Thereafter, 0.0267 g (0.0989 mmol) of potassium persulfate and 0.38 g of ion-exchanged water were added, and then potassium persulfate was dissolved to prepare the third stage monomer aqueous solution.

Then, the temperature of a second stage reaction mixture (polymer particles before crosslinking) was raised in an oil bath at 125° C., and 267 g of water was extracted to the outside of the system while refluxing n-heptane by azeotropic distillation of n-heptane and water. Subsequently, 0.0884 g (0.5075 mmol) of ethylene glycol diglycidyl ether was added as a crosslinking agent, and also, the above-mentioned third stage monomer aqueous solution was added, and thereafter, the mixture was maintained at 83° C. for 2 hours to obtain a dispersion liquid of the polymer particles after crosslinking.

Thereafter, the temperature of the dispersion liquid of the polymer particles after crosslinking was raised in an oil bath at 125° C., water was extracted to the outside of the system until the temperature inside the flask reached 90° C. while refluxing n-heptane by azeotropic distillation of n-heptane and water, and thereafter drying was performed by evaporating n-heptane to obtain a polymerization product. This polymerization product was passed through a sieve having the opening of 850 μm to obtain 209.29 g of water-absorbent resin particles in the form of aggregated spherical particles. The median particle diameter of the water-absorbent resin particles was 372 μm.

Comparative Example 3

210.70 g of water-absorbent resin particles was obtained in the same manner as in Comparative Example 1 except that, in Comparative Example 3, the amount of water extracted after second stage polymerization was changed from 245 g to 241 g, the details of a third stage monomer aqueous solution were changed, and the amount of water extracted after third stage polymerization was changed from 204 g to 32 g. The third stage monomer aqueous solution was prepared as follows: 33.4 g (acrylic acid: 0.37 mol) of an aqueous solution of 80.5% by mass acrylic acid was put to a triangular flask having the volume of 500 mL; while cooling from the outside, 37.7 g of an aqueous solution of 30% by mass sodium hydroxide was added dropwise to neutralize 75 mol % of acrylic acid; and 0.0267 g (0.0989 mmol) of potassium persulfate and 0.38 g of ion-exchanged water were added, and then potassium persulfate was dissolved. The median particle diameter of the water-absorbent resin particles was 378 μm.

Example 4

201.46 g of water-absorbent resin particles (in the form of aggregated spherical particles) was obtained in the same manner as in Example 1 except that the details of a third stage monomer aqueous solution were changed in Example 4. The third stage monomer aqueous solution was prepared as follows: 22.3 g (acrylic acid: 0.25 mol) of an aqueous solution of 80.5% by mass acrylic acid was put to a triangular flask having the volume of 500 mL; while cooling from the outside, 25.1 g of an aqueous solution of 30% by mass sodium hydroxide was added dropwise to neutralize 75 mol % of acrylic acid; and 0.0178 g (0.0658 mmol) of potassium persulfate and 0.30 g of ion-exchanged water were added, and then potassium persulfate was dissolved. The median particle diameter of the water-absorbent resin particles was 387 μm.

Comparative Example 4

200.02 g of water-absorbent resin particles was obtained in the same manner as in Comparative Example 1 except that, in Comparative Example 4, the details of a third stage monomer aqueous solution were changed, and the amount of water extracted after third stage polymerization was changed from 204 g to 22 g. The third stage monomer aqueous solution was prepared as follows: 22.3 g (acrylic acid: 0.25 mol) of an aqueous solution of 80.5% by mass acrylic acid was put to a triangular flask having the volume of 500 mL; while cooling from the outside, 25.1 g of an aqueous solution of 30% by mass sodium hydroxide was added dropwise to neutralize 75 mol % of acrylic acid; and 0.0178 g (0.0658 mmol) of potassium persulfate and 0.30 g of ion-exchanged water were added, and then potassium persulfate was dissolved. The median particle diameter of the water-absorbent resin particles was 381 μm.

Example 5

173.68 g of water-absorbent resin particles (in the form of aggregated spherical particles) was obtained in the same manner as in Example 1 except that, in Example 5, the amount of water extracted after second stage polymerization was changed from 267 g to 245 g, and the details of a third stage monomer aqueous solution were changed. The third stage monomer aqueous solution was prepared as follows: 0.2 g (acrylic acid: 0.002 mol) of an aqueous solution of 80.5% by mass acrylic acid was put to a triangular flask having the volume of 500 mL; while cooling from the outside, 0.3 g of an aqueous solution of 30% by mass sodium hydroxide was added dropwise to neutralize 75 mol % of acrylic acid; and 0.000178 g (0.00066 mmol) of potassium persulfate and 0.84 g of ion-exchanged water were added, and then potassium persulfate was dissolved. The median particle diameter of the water-absorbent resin particles was 356 μm.

Comparative Example 5

172.62 g of water-absorbent resin particles was obtained in the same manner as in Comparative Example 1 except that, in Comparative Example 5, the details of a third stage monomer aqueous solution were changed, and the amount of water extracted after third stage polymerization was changed from 204 g to 0.2 g. The third stage monomer aqueous solution was prepared as follows: 0.2 g (acrylic acid: 0.002 mol) of an aqueous solution of 80.5% by mass acrylic acid was put to a triangular flask having the volume of 500 mL; while cooling from the outside, 0.3 g of an aqueous solution of 30% by mass sodium hydroxide was added dropwise to neutralize 75 mol % of acrylic acid; and 0.000178 g (0.00066 mmol) of potassium persulfate and 0.84 g of ion-exchanged water were added, and then potassium persulfate was dissolved. The median particle diameter of the water-absorbent resin particles was 366 μm.

Example 6

193.20 g of water-absorbent resin particles (in the form of aggregated spherical particles) was obtained in the same manner as in Example 3 except that the details of a third stage monomer aqueous solution were changed in Example 6. The third stage monomer aqueous solution was obtained by mixing 22.1 g (0.31 mol) of acrylamide, 0.0177 g (0.0655 mmol) of potassium persulfate, 0.0884 g (0.5075 mmol) of ethylene glycol diglycidyl ether (crosslinking agent), and 22.80 g of ion-exchanged water. The median particle diameter of the water-absorbent resin particles was 385 μm.

Comparative Example 6

198.28 g of water-absorbent resin particles (in the form of aggregated spherical particles) was obtained in the same manner as in Comparative Example 1 except that, in Comparative Example 6, the amount of water extracted after second stage polymerization was changed from 245 g to 237 g, the details of a third stage monomer aqueous solution were changed, and the amount of water extracted after third stage polymerization was changed from 204 g to 21 g. The third stage monomer aqueous solution was obtained by mixing 22.1 g (0.31 mol) of acrylamide, 0.0177 g (0.0655 mmol) of potassium persulfate, and 27.22 g of ion-exchanged water. The median particle diameter of the water-absorbent resin particles was 413 μm.

Example 7

227.32 g of water-absorbent resin particles (in the form of aggregated spherical particles) was obtained in the same manner as in Example 1 except that, in Example 7, the amount of water extracted after second stage polymerization was changed from 267 g to 269 g, and the details of a third stage monomer aqueous solution were changed.

First, the production was performed in the same manner as in Example 1 up to the second stage polymerization.

After the second stage polymerization, the temperature of a second stage reaction mixture (polymer particles before surface crosslinking) was raised in an oil bath at 125° C., and 269 g of water was extracted to the outside of the system while refluxing n-heptane by azeotropic distillation of n-heptane and water. Subsequently, 0.0884 g (0.5075 mmol) of ethylene glycol diglycidyl ether was added as a surface crosslinking agent, and thereafter the mixture was maintained at 83° C. for 2 hours to obtain a dispersion liquid of the polymer particles after surface crosslinking.

Subsequently, as the third stage monomer aqueous solution, 88 g of a mixed solution A (polyol aqueous solution) was prepared by mixing 4.4 g of polyether polyol (DKS Co., Ltd., DK POLYOL 3817) and 83.6 g of distilled water, and 31.14 g of a mixed solution B (isocyanate acetone solution) was prepared by mixing 3.12 g of Tolylene-2,4-diisocyanate and 28.02 g of acetone.

Then, the above-mentioned dispersion liquid of the polymer particles after surface crosslinking was maintained at 83° C. for 2 hours. Thereafter, the above-mentioned mixed solution A was added to the dispersion liquid of the polymer particles after surface crosslinking, and then the mixture was stirred at 80° C. for 30 minutes. Subsequently, after adding the above-mentioned mixed solution B, the mixture was stirred at 80° C. for 60 minutes, and a third stage reaction mixture was obtained by advancing a sequential polymerization reaction (third stage polymerization) on the surface of the polymer particles for polymerization of polyurethane.

After the third stage polymerization, the temperature of the third stage reaction mixture was raised in an oil bath at 125° C., water and acetone were extracted to the outside of the system until the temperature inside the flask reached 90° C. while evaporating n-heptane by azeotropic distillation of n-heptane and water, and thereafter drying was performed by evaporating n-heptane to obtain a polymerization product. This polymerization product was passed through a sieve having the opening of 850 μm to obtain 227.32 g of water-absorbent resin particles in the form of aggregated spherical particles. The median particle diameter of the water-absorbent resin particles was 373 μm.

Comparative Example 7

Water-absorbent resin particles were produced in the same manner as in Example 7 except that, in Comparative Example 7, after obtaining a second stage reaction mixture (polymer particles before surface crosslinking), third stage polymerization and surface crosslinking were performed in this order instead of performing surface crosslinking before the third stage polymerization.

First, the production was performed in the same manner as in Example 1 up to second stage polymerization.

After the second stage polymerization, the temperature of the second stage reaction mixture (polymer particles before surface crosslinking) was raised in an oil bath at 125° C., and 245 g of water was extracted to the outside of the system while refluxing n-heptane by azeotropic distillation of n-heptane and water.

Subsequently, as the third stage monomer aqueous solution, 88 g of a mixed solution A(polyol aqueous solution) was prepared by mixing 4.4 g of polyether polyol (DKS Co., Ltd., DK POLYOL 3817) and 83.6 g of distilled water, and 31.14 g of a mixed solution B (isocyanate acetone solution) was prepared by mixing 3.12 g of Tolylene-2,4-diisocyanate and 28.02 g of acetone.

Thereafter, the above-mentioned mixed solution A was added to the second stage reaction mixture (reaction mixture after extraction of water), and then the mixture was stirred at 80° C. for 30 minutes. Subsequently, after adding the above-mentioned mixed solution B, the mixture was stirred at 80° C. for 60 minutes, and a third stage reaction mixture was obtained by advancing a sequential polymerization reaction (third stage polymerization) on the surface of the polymer particles for polymerization of polyurethane.

After the third stage polymerization, the temperature of the third stage reaction mixture was raised in an oil bath at 125° C., and 47 g of water and acetone were extracted to the outside of the system while refluxing n-heptane by azeotropic distillation of n-heptane and water.

Thereafter, 0.0884 g (0.5075 mmol) of ethylene glycol diglycidyl ether was added as a surface crosslinking agent, and thereafter the mixture was maintained at 83° C. for 2 hours.

Then, drying was performed by evaporating n-heptane by raising the temperature in an oil bath at 125° C. to obtain a polymerization product. This polymerization product was passed through a sieve having the opening of 850 μm to obtain 230.16 g of water-absorbent resin particles in the form of aggregated spherical particles. The median particle diameter of the water-absorbent resin particles was 450 μm.

Example 8

In Example 8, water-absorbent resin particles were produced after producing polymer particles by an aqueous solution polymerization method.

A round-bottomed cylindrical separable flask with the inner diameter of 11 cm and the volume of 2 L equipped with a reflux cooling device, a dropping funnel, a nitrogen gas introduction tube, and a stirrer (a stirrer blade having two stages of four inclined paddle blades having the blade diameter of 5 cm) was prepared. 509.71 g (7.07 mol) of 100% acrylic acid was put to this separable flask. While stirring this acrylic acid, 436.47 g of ion-exchanged water was added into the separable flask. Thereafter, 444.68 g of 48% by mass sodium hydroxide was added dropwise in an ice bath (1° C.) to prepare 1390.86 g of a partially neutralized acrylic acid solution (neutralization rate: 75.44 mol %) having the monomer concentration of 45.08% by mass. The present operation was performed again to prepare a total of 2781.72 g of the partially neutralized acrylic acid solution.

406.89 g of ion-exchanged water and 2.90 g (5.576 mmol) of polyethylene glycol diacrylate (internal crosslinking agent, n=9) were added to 2781.72 g of the above-mentioned partially neutralized acrylic acid solution to obtain a reaction solution (monomer aqueous solution). Subsequently, this reaction solution was replaced with nitrogen gas for 30 minutes under a nitrogen gas atmosphere. Subsequently, the above-mentioned reaction solution was supplied to a stainless steel double arm kneader equipped with a thermometer, a nitrogen blow tube, an openable and closable lid, two sigma-shaped blades, and a jacket, and then the system was replaced with nitrogen gas while maintaining the reaction solution at 30° C. Subsequently, while stirring the reaction solution, 92.63 g (7.780 mmol) of an aqueous solution of 2.0% by mass sodium persulfate and 15.85 g of an aqueous solution of 0.5% by mass L-ascorbic acid were added. The temperature began to rise after about 1 minute, and polymerization started. The temperature was 93° C. after 6 minutes as the maximum temperature during the polymerization. Thereafter, stirring was continued while maintaining the jacket temperature at 60° C., and 60 minutes after the start of the polymerization, a hydrogel which was a first stage polymerization reaction product was taken out. The obtained hydrogel was sequentially injected into a meat chopper 12VR-750SDX manufactured by Kiren Royal Co., Ltd. and fragmented. The diameter of a hole in a plate located at the tip of the meat chopper was 6.4 mm.

This fragmented granular hydrogel was spread on a wire mesh having an opening of 0.8 cm×0.8 cm, and then dried with hot air at 160° C. for 60 minutes to obtain a dried product.

Subsequently, the dried product was pulverized using a Centrifugal Mill (ZM 200 manufactured by Retsch GmbH, screen aperture 1 mm, 12000 rpm) to obtain an amorphous crushed resin powder A. Furthermore, this resin powder A was classified with a wire mesh having the opening of 850 μm, a wire mesh having the opening of 250 μm, and a wire mesh having the opening of 180 μm to obtain a resin powder B which was a fraction that passed through the wire mesh having the opening of 850 μm but did not pass through the wire mesh having the opening of 250 μm.

A round-bottomed cylindrical separable flask with the inner diameter of 11 cm and the volume of 2 L equipped with a reflux cooling device, a dropping funnel, a nitrogen gas introduction tube, and a stirrer (a stirrer blade having two stages of four inclined paddle blades having the blade diameter of 5 cm) was prepared. 100 g of the above-mentioned resin powder B was put to this separable flask, and 560 g of n-heptane was added as a hydrocarbon dispersion medium.

Thereafter, after raising the temperature of the separable flask to 83° C. in an oil bath at 125° C., 0.040 g (0.230 mmol) of ethylene glycol diglycidyl ether was added as a surface crosslinking agent, and thereafter the mixture was maintained at 83° C. for 2 hours to obtain a dispersion liquid of the polymer particles after surface crosslinking.

Subsequently, 10.1 g (acrylic acid: 0.11 mol) of an aqueous solution of 80.5% by mass acrylic acid was put to a triangular flask having the volume of 500 mL. Subsequently, while cooling from the outside, 11.4 g of an aqueous solution of 30% by mass sodium hydroxide was added dropwise to neutralize 75 mol % of acrylic acid. Thereafter, 0.00810 g (0.0300 mmol) of potassium persulfate was added, and then potassium persulfate was dissolved to prepare a second stage monomer aqueous solution.

Then, the above-mentioned dispersion liquid of the polymer particles after surface crosslinking was maintained at 83° C. for 2 hours, and then air-cooled to 50° C. Subsequently, the total amount of the above-mentioned second stage monomer aqueous solution was added to the dispersion liquid of the polymer particles after surface crosslinking to obtain a reaction solution. Then, the inside of the system was sufficiently replaced with nitrogen while stirring the reaction solution, and then the reaction solution was maintained at 45° C. for 30 minutes. Furthermore, the separable flask was immersed in a water bath at 75° C. to raise the temperature, and second stage polymerization was performed for 15 minutes to obtain a second stage reaction mixture.

After the second stage polymerization, the temperature of the second stage reaction mixture was raised in an oil bath at 125° C., water was extracted to the outside of the system until the temperature inside the flask reached 90° C. while refluxing n-heptane by azeotropic distillation of n-heptane and water, and thereafter drying was performed by evaporating n-heptane to obtain a polymerization product. This polymerization product was passed through a sieve having the opening of 850 μm to obtain 109.19 g of water-absorbent resin particles. The median particle diameter of the water-absorbent resin particles was 460 μm.

Comparative Example 8

Water-absorbent resin particles were produced in the same manner as in Example 8 except that, in Comparative Example 8, after obtaining a resin powder B, second stage polymerization and surface crosslinking were performed in this order instead of performing surface crosslinking before the second stage polymerization.

First, in the same manner as in Example 8, after obtaining the resin powder B, 100 g of the resin powder B and 560 g of n-heptane (hydrocarbon dispersion medium) were mixed in a separable flask.

Thereafter, the temperature of the separable flask was raised to 83° C. in an oil bath at 125° C., and then air-cooled to 50° C. to obtain a dispersion liquid A of polymer particles before surface crosslinking.

Subsequently, the total amount of a second stage monomer aqueous solution similar to that in Example 8 was added to the dispersion liquid A of polymer particles before surface crosslinking to obtain a reaction solution. Then, the inside of the system was sufficiently replaced with nitrogen while stirring the reaction solution, and then the reaction solution was maintained at 45° C. for 30 minutes. Furthermore, the separable flask was immersed in a water bath at 75° C. to raise the temperature, and the second stage polymerization was performed for 15 minutes to obtain a second stage reaction mixture.

After the second stage polymerization, the temperature of the second stage reaction mixture was raised in an oil bath at 125° C., and 9 g of water was extracted to the outside of the system while refluxing n-heptane by azeotropic distillation of n-heptane and water to obtain a dispersion liquid B of polymer particles before surface crosslinking.

Then, 0.040 g (0.230 mmol) of ethylene glycol diglycidyl ether as a surface crosslinking agent was added to the dispersion liquid B of polymer particles before surface crosslinking, and thereafter the mixture was maintained at 83° C. for 2 hours to obtain a dispersion liquid of the polymer particles after surface crosslinking.

Thereafter, drying was performed by evaporating n-heptane by raising the temperature of the dispersion liquid of the polymer particles after surface crosslinking in an oil bath at 125° C. to obtain a polymerization product. This polymerization product was passed through a sieve having the opening of 850 μm to obtain 230.16 g of water-absorbent resin particles in the form of aggregated spherical particles. The median particle diameter of the water-absorbent resin particles was 454 μm.

<Median Particle Diameter>

The above-mentioned median particle diameter of the water-absorbent resin particles was measured by the following procedure. The particle size distribution of 5 g of the water-absorbent resin particles was measured using an Automated Sonic Sieving Particle Size Analyzer (Robot Sifter RPS-205, manufactured by SEISHIN ENTERPRISE Co., Ltd.), JIS standard sieves having the openings of 850 μm, 710 μm, 600 μm, 500 μm, 400 μm, 300 μm, 250 μm, and 150 μm, and a tray. The relationship between the opening of the sieve and the integrated value of the mass percentage of the particles remaining on the sieve was plotted on a logarithmic probability paper by integrating the masses of the particles remaining on the sieve in the order from the one having the largest particle diameter with respect to this particle size distribution. By connecting the plots on the logarithmic probability paper with a straight line, the particle diameter corresponding to the cumulative mass percentage of 50% by mass was obtained as the median particle diameter.

<Water Absorption Amount Under Load>

The water absorption amount (room temperature, 25° C.±2° C.) of physiological saline under load (under pressurization) of the water-absorbent resin particles was measured using a measurement device Y shown in FIG. 1. The measurement device Y is constituted of a burette unit 61, a conduit 62, a measurement table 63, and a measurement unit 64 placed on the measurement table 63. The burette unit 61 has a burette 61a extending in a vertical direction, a rubber stopper 61b disposed at the upper end of the burette 61a, a cock 61c disposed at the lower end of the burette 61a, an air introduction tube 61d of which one end extends into the burette 61a in the vicinity of the cock 61c, and a cock 61e disposed on the other end side of the air introduction tube 61d. The conduit 62 is attached between the burette unit 61 and the measurement table 63. The inner diameter of the conduit 62 is 6 mm. At the central portion of the measurement table 63, a hole having the diameter of 2 mm is formed, and the conduit 62 is connected. The measurement unit 64 has a cylinder 64a (made of acrylic resin (plexiglass)), a nylon mesh 64b adhered to the bottom of the cylinder 64a, and a weight 64c. The inner diameter of the cylinder 64a is 20 mm. The opening of the nylon mesh 64b is 57 μm (255 mesh). Then, at the time of measurement, water-absorbent resin particles 65 to be measured are uniformly scattered on the nylon mesh 64b. The weight 64c has the diameter of 19 mm, and the mass of the weight 64c is 120 g. The weight 64c is placed on the water-absorbent resin particles 65, and can apply the load of 4.14 kPa to the water-absorbent resin particles 65.

After putting 0.100 g of the water-absorbent resin particles 65 in the cylinder 64a of the measurement device Y, the weight 64c was placed and the measurement was started. Since the same volume of air as physiological saline absorbed by the water-absorbent resin particles 65 is quickly and smoothly supplied to the inside of the burette 61a from the air introduction tube, the amount of reduction in the water level of physiological saline inside the burette 61a corresponds to the amount of physiological saline absorbed by the water-absorbent resin particles 65. A scale of the burette 61a is engraved from top to bottom in increments of 0 mL to 0.5 mL; as a water level of physiological saline, a scale Va of the burette 61a before the start of water absorption and a scale Vb of the burette 61a after 60 minutes from the start of water absorption were read; and a water absorption amount under the load and an increase rate were calculated by the following formula. The results are shown in Table 1.

Water absorption amount under load[mL/g]=($Vb-Va$)/0.1

Increase rate of water absorption amount under load [%]={(water absorption amount of Example−water absorption amount of Comparative Example)/(water absorption amount of Comparative Example)}×100

<Damage Rate>

Fifteen (about 100 g) spherical alumina balls (alumina ball HD-15, manufactured by Nikkato Corporation) having the diameter of 15 mm, and 10 g of the water-absorbent resin particles were put to an alumina pot for ball mills having the volume of 400 mL, and the water-absorbent resin particles were pulverized for 15 minutes at the rotation speed of 140 rpm. Thereafter, using a JIS standard sieve having the opening of 150 μm, the pulverized product was manually passed through this sieve for 2 minutes. Based on the total mass $W_A$ of the particles that passed through the sieve and the total mass $W_B$ of the particles that did not pass through the sieve, a damage rate and an increase rate were calculated by the following formulas. The results are shown in Table 1.

Damage rate[% by mass]={$W_A/(W_A+W_B)$}×100

Increase rate of damage rate[%]={(damage rate of Example−damage rate of Comparative Exampled/(damage rate of Comparative Example)}×100

TABLE 1

| | Polymerization method of polymer particle | Polymer of outermost surface | Amount of monomer when polymerizing outermost surface [mol] | Water absorption amount under load | Damage rate |
|---|---|---|---|---|---|
| Example 1 | Reverse phase suspension polymerization | Acrylic acid polymer | 1.25 | 17 mL/g | 3.9% |
| Comparative Example 1 | | | | 3 mL/g | 5.0% |
| Increase rate | | | | 467% | 22% |
| Example 2 | | | 0.5 | 22 mL/g | 6.8% |
| Comparative Example 2 | | | | 20 mL/g | 8.2% |
| Increase rate | | | | 10% | 17% |

TABLE 1-continued

| | Polymerization method of polymer particle | Polymer of outermost surface | Amount of monomer when polymerizing outermost surface [mol] | Water absorption amount under load | Damage rate |
|---|---|---|---|---|---|
| Example 3 | | | 0.37 | 25 mL/g | 5.0% |
| Comparative Example 3 | | | | 21 mL/g | 7.4% |
| Increase rate | | | | 19% | 32% |
| Example 4 | | | 0.25 | 13 mL/g | 3.3% |
| Comparative Example 4 | | | | 12 mL/g | 6.4% |
| Increase rate | | | | 8% | 48% |
| Example 5 | | | 0.002 | 10 mL/g | 2.9% |
| Comparative Example 5 | | | | 9 mL/g | 4.2% |
| Increase rate | | | | 11% | 31% |
| Example 6 | | Acrylamide polymer | 0.31 | 26 mL/g | 4.3% |
| Comparative Example 6 | | | | 26 mL/g | 6.7% |
| Increase rate | | | | 0% | 36% |
| Example 7 | | Polyurethane | | 23 mL/g | 1.0% |
| Comparative Example 7 | | | | 18 mL/g | 1.7% |
| Increase rate | | | | 28% | 41% |
| Example 8 | Aqueous solution polymerization | Acrylic acid polymer | 0.11 | 24 mL/g | 2.0% |
| Comparative Example 8 | | | | 20 mL/g | 2.5% |
| Increase rate | | | | 20% | 20% |

REFERENCE SIGNS LIST

61 ... burette unit, 61a ... burette, 61b ... rubber stopper, 61c, 61e ... cock, 61d ... air introduction tube, 62 ... conduit, 63 ... measurement table, 64 ... measurement unit, 64a ... cylinder, 64b ... nylon mesh, 64c ... weight, 65 ... water-absorbent resin particle, Y ... measurement device.

The invention claimed is:

1. A water-absorbent resin particle comprising:
   a surface-crosslinked polymer particle; and
   a polymer disposed on at least a part of a surface of the polymer particle, wherein:
   the polymer particle has a structural unit derived from an ethylenically unsaturated monomer, the ethylenically unsaturated monomer of the polymer particle includes at least one selected from the group consisting of (meth) acrylic acid and salts thereof,
   the polymer has a structural unit derived from an ethylenically unsaturated monomer, the ethylenically unsaturated monomer of the polymer consisting of at least one selected from the group consisting of (meth) acrylic acid and salts thereof, and
   an amount of the ethylenically unsaturated monomer of the polymer is 10 to 100 mol with respect to 100 mol of a total amount of monomer for obtaining the polymer particle.

2. The water-absorbent resin particle according to claim 1, wherein a ratio of (meth) acrylic acid and salts thereof in the polymer particle is 70 to 100 mol % with respect to the total amount of the monomer for obtaining the polymer particle.

3. The water-absorbent resin particle according to claim 1, wherein a degree of neutralization in the ethylenically unsaturated monomer of the polymer particle is 50 to 90 mol %.

4. A method for producing the water-absorbent resin particles according to claim 1, the method comprising polymerizing the monomer on at least a part of a surface of a surface-crosslinked polymer particle to obtain a polymer.

* * * * *